(12) United States Patent
Gaemers et al.

(10) Patent No.: US 7,368,597 B2
(45) Date of Patent: *May 6, 2008

(54) CARBONYLATION PROCESS USING METAL-POLYDENTATE LIGAND CATALYSTS

(75) Inventors: Sander Gaemers, East Riding of Yorkshire (GB); John Glenn Sunley, Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/555,739

(22) PCT Filed: May 5, 2004

(86) PCT No.: PCT/GB2004/001900

§ 371 (c)(1),
(2), (4) Date: Nov. 7, 2005

(87) PCT Pub. No.: WO2004/101487

PCT Pub. Date: Nov. 25, 2004

(65) Prior Publication Data

US 2007/0010687 A1    Jan. 11, 2007

(30) Foreign Application Priority Data

May 14, 2003   (GB) ................ 0311092.1

(51) Int. Cl.
*C07C 51/12*   (2006.01)
(52) U.S. Cl. ...................... 562/519; 562/517
(58) Field of Classification Search ............... 562/519, 562/517

See application file for complete search history.

(56) References Cited

U.S. PATENT DOCUMENTS

| 4,102,920 A | | 7/1978 | Bartish |
| 5,284,964 A | * | 2/1994 | Pressman et al. ........... 558/260 |
| 5,352,813 A | * | 10/1994 | Cavell et al. ................ 556/21 |
| 6,482,958 B2 | * | 11/2002 | Junghans et al. ............. 549/6 |

FOREIGN PATENT DOCUMENTS

| DE | 44 26 577 A | 2/1996 |
| EP | 1 099 681 A2 | 5/2001 |
| EP | 1 099 681 A3 | 1/2003 |

* cited by examiner

*Primary Examiner*—Yvonne Eyler
*Assistant Examiner*—Sudhakar Katakam
(74) *Attorney, Agent, or Firm*—Nixon & Vanderhye

(57) ABSTRACT

A process for the liquid phase carbonylation of an alcohol and/or a reactive derivative thereof in the presence of hydrogen in which there is employed a catalyst comprising rhodium of iridium coordinated with a polydentate ligand.

50 Claims, No Drawings

CARBONYLATION PROCESS USING METAL-POLYDENTATE LIGAND CATALYSTS

This application is the U.S. National Phase of International Application PCT/GB04/001900 filed 5 May 2004 which designated the U.S. PCT/GB04/001900 claims priority to British Application No. 0311092.1 filed 14 May 2003. The entire content of these applications are incorporated herein by reference.

The present invention relates in general to a process for the liquid phase carbonylation of an alcohol and/or a reactive derivative thereof. In particular the present invention relates to the liquid phase carbonylation of an alcohol and/or a reactive derivative thereof in the presence of hydrogen and a catalyst comprising rhodium or iridium coordinated with a polydentate ligand.

Preparation of carboxylic acids by rhodium-catalysed carbonylation processes is known and is described, for example, in EP-A-0632006 and U.S. Pat. No. 4,670,570.

EP-A-0632006 discloses a process for the liquid phase carbonylation of methanol or a reactive derivative thereof which process comprises contacting carbon monoxide with a liquid reaction composition comprising methanol or a reactive derivative thereof, a halogen promoter and a rhodium catalyst system comprising a rhodium component and a bidentate phosphorus-sulphur ligand, the ligand comprising a phosphorus dative centre linked to a sulphur dative or anionic centre by a substantially unreactive backbone structure comprising two connecting carbon atoms or a connecting carbon and a connecting phosphorus atom.

Preparation of carboxylic acids by iridium-catalysed carbonylation processes is known and is described, for example in EP-A-0786447, EP-A0643034 and EP-A-0752406.

EP-A-0643034 describes a process for the production of acetic acid by carbonylation of methanol or a reactive derivative thereof which process comprises contacting methanol or a reactive derivative thereof with carbon monoxide in a liquid reaction composition in a carbonylation reactor characterised in that the liquid composition comprises (a) acetic acid, (b) an iridium catalyst, (c) methyl iodide, (d) at least a finite quantity of water, (e) methyl acetate and (f) as promoter, at least one of ruthenium and osmium.

The use of bidentate chelating phosphorus or arsenic ligands in carbonylation processes is known, for example, from GB 2,336,154, U.S. Pat. No. 4,102,920 and U.S. Pat. No. 4,102,921.

GB 2,336,154 describes a process for the liquid-phase carbonylation of an alcohol and/or a reactive derivative thereof to produce a carboxylic acid in the presence of a bidentate ligand of formula $R^1R^2X—Z—YR^5R^6$, wherein X and Y are independently N, P, As, Sb or Bi, and Z is a divalent linking group.

U.S. Pat. No. 4,102,920 describes a process for the carbonylation of alcohols, esters, ethers and organo halides in the presence of a rhodium complex with a polydentate phosphine or arsenic chelating ligand. U.S. Pat. No. 4,102,921 describes a similar process in the presence of an iridium complex with a polydentate phosphine or arsenic chelating ligand.

The carbonylation of methanol to produce acetic acid, the presence of hydrogen is known to result in the formation of undesirable liquid by-products such as acetaldehyde, ethanol and propionic acid. Propionic acid requires an expensive and energy intensive distillation column to separate it from the acetic acid product. Furthermore acetaldehyde can undergo a series of condensation and other reactions to yield, eventually, higher organic iodide compounds. Some of these materials, especially, for example, hexyl iodide, are difficult to remove by conventional distillation and further treatment steps are sometimes necessary to give acetic acid of sufficient purity. EP-A-0 849 251, which describes an iridium catalysed process for the carbonylation of methanol to acetic acid, states that the amount of hydrogen in the carbon monoxide feed is preferably less than 1 mol % and the hydrogen partial pressure in the reactor is preferably less than 1 bar. Similarly, EP-A-0 728 727, which describes a rhodium catalysed process for the carbonylation of methanol to acetic acid, states that the hydrogen partial pressure in the reactor is preferably less than 2 bar.

It has also been found that, using certain rhodium catalysts for methanol carbonylation, the presence of hydrogen in the carbon monoxide feed leads to the production of ethanol and acetaldehyde with only minor amounts of acetic acid being produced.

U.S. Pat. No. 4,727,200, for example, describes a process for the homologation of an alcohol by reaction with synthesis gas using a rhodium-containing catalyst system. The major product formed with a synthesis gas feed is ethanol, acetic acid being a relatively minor by-product.

Moloy et al. (Organometallics, 1989, 8, pp 2883-2893) describe a process for the rhodium-catalysed reductive carbonylation of methanol utilising synthesis gas in the presence of a diphosphine ligand to produce high levels of acetaldehyde. Addition of ruthenium to the catalyst favours hydrogenation to produce ethanol.

Thus, there remains a need for an improved process for the production of carboxylic acids and/or the alcohol esters of carboxylic acids by the catalytic carbonylation of an alcohol and/or a reactive derivative thereof. In particular there remains a need for a carbonylation process which is tolerant towards the presence of hydrogen in that only small quantities of or no liquid hydrogenation by-products are produced.

It has now been found that an improved carbonylation process may be achieved by employing a catalyst comprising rhodium or iridium coordinated with a polydentate ligand wherein said ligand has a bite angle of at least 145° or is coordinated to the rhodium or iridium metal in a rigid structural conformation. Advantageously, the catalysts employed in the process of the present invention have been found to have improved tolerance of hydrogen present in the carbonylation process in that no or small quantities of liquid by-products are formed in the process. In addition, the metal-polydentate ligand complexes according to the present invention may have higher stability in the carbonylation process than non-rigid metal-ligand complexes or complexes having ligands with a bite angle of less than 145°. Furthermore, the process of the present invention can be carried out in the absence of a conventional catalyst stabiliser compound such as lithium iodide.

Accordingly, the present invention provides a process for the production of a carboxylic acid and/or the alcohol ester of a carboxylic acid, which process comprises carbonylating an alcohol and/or a reactive derivative thereof with carbon monoxide in a liquid reaction composition in a carbonylation reactor, said liquid reaction composition comprising said alcohol and/or a reactive derivative thereof, a carbonylation catalyst and an alkyl halide co-catalyst and optionally a finite concentration of water, wherein said catalyst comprises at least one of rhodium or iridium which is coordinated with a polydentate ligand wherein said polydentate ligand has a bite angle of at least 145° or forms a rigid Rh or Ir metal-ligand complex and wherein said polydentate ligand comprises at least two coordinating groups which, independently contain P, N, As or Sb as the coordinating atom of at least two of the co-ordinating groups and wherein in said process there is maintained hydrogen at a hydrogen: CO mole ratio of at least 1:100 and/or the carbon monoxide feed to the carbonylation reactor contains at least 1 mol % hydrogen.

The polydentate ligand comprises at least two coordinating groups which, independently, contain P, N, As or Sb as the coordinating atom (donor atom) in at least two of the co-ordinating groups. The two coordinating groups may be represented, respectively, as L1 and L2.

The polydentate ligand, when complexed with the rhodium or iridium metal centre (atom), will form a ring structure comprising the metal atom, the coordinating P, N, As or Sb atoms and the ligand backbone. "Rigid metal-ligand complex", as used herein, means that the ring structure has a rigid conformation. The degree of rigidity of a metal-ligand complex may be derived by the skilled man based on the structure of the ligand and its expected bonding configuration. Rigidity may be defined in general terms by consideration of the structure of the ligand-metal complex formed, or, for a more accurate definition, may be defined mathematically, for example in terms of the "flexibility range" of the ligand. "Flexibility range" as used herein, is defined as the range of bite angles accessible for the L1-M-L2 angle (wherein the L1-M-L2 angle is the angle formed by the two co-ordinating groups and the metal centre, M, wherein M is Rh or Ir), for example, within 3 kcal/mol of the minimum energy. The bite angle and flexibility range for a bidentate ligand may be derived from the potential energy diagram calculated according to the method of Casey et al. in Israel Journal of Chemistry, Vol. 30 (1990), p. 299-304, the contents of which are herein incorporated by reference. Preferably, for the catalysts of the present invention, the flexibility range is less than 40°, preferably less than 30°. Similar calculations may be used to define the flexibility range for non-bidentate ligands.

Preferably, the co-ordinating groups, L1 and L2 each contain phosphorus as the coordinating atom. Such phosphorus-containing groups, referred to hereinafter as P1 and P2, preferably have general formula $R^1R^2P$ and $R^3R^4P$, wherein $R^1$, $R^2$, $R^3$ and $R^4$ are each independently selected from unsubstituted or substituted alkenyl groups, alkyl groups and aryl groups, especially phenyl groups. Preferably $R^1$, $R^2$, $R^3$ and $R^4$ are each a phenyl group. One or more of the phenyl groups may be substituted or unsubstituted. For example, each of P1 and P2 may be a diphenylphosphine group ($PPh_2$). Alternatively, one or more of the $R^1$, $R^2$, $R^3$ and $R^4$ phenyl groups in the P1 and P2 groups may be substituted. Suitably, the phenyl groups may be substituted at one or more of the ortho positions by at least one group selected from alkyl, aryl and alkyloxy (OR) groups. Particularly preferred ortho-substituents are Me, $CF_3$, Et, iso-Pr and OMe.

To improve the solubility of the polydentate ligand and hence the catalyst in the liquid reaction composition one or more of the $R^1$, $R^2$, $R^3$, and $R^4$ groups on the co-ordinating groups may be substituted with one or more hydrophilic and/or polar groups. Examples of such groups include $-CO_2H$, $-CO_2Me$, $-OH$, $-SO_3H$, $-SO_3Na$, $-NH_2$, $-NH_3^+$ and $-NR_2H^+$.

The rigid conformation of a polydentate metal-ligand complex will be the direct result of the ligand structure. In particular, where the polydentate ligand is a bidentate ligand, the ligand should have hindered rotation along the ligand backbone. The ligand backbone, as defined herein, is the part or parts of the ligand which will form the ring structure (comprising the metal atom and the coordinating (donor) atoms) in the metal-ligand complex. For example, the rigid conformation may be the result of a vinylic or an aromatic backbone between the coordinating groups L1 and L2, which hinders or prevents rotation of the ligand backbone. Alternatively, or additionally, the ligand-metal complex may be rigid due to steric effects that hinder rotation of the ligand backbone.

Suitable rigid bidentate phosphine-containing ligands include those of general structures 1 to 3 below; wherein P1 and P2 are $R^1R^2P$ and $R^3R^4P$ respectively and wherein $R^1$—$R^4$ are as defined above:

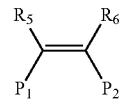

Structure (1)

1,2-vinyl backbone.

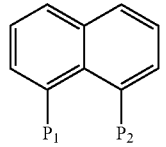

Structure (2)

1,8-naphthalene backbone

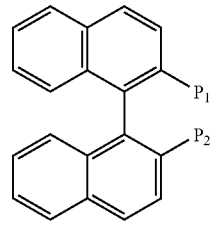

Structure (3)

1,1'-binaphthalene backbone

Each of structures (1 to 3) will form metal-bidentate ligand complexes with a rigid conformation. For example, ligands of general structure 1 will form five-membered rings with the metal centre, the structures of which are rigid due to the vinylic backbone. $R_5$ and $R_6$ in structure 1 may, independently, be selected from H, alkyl and aryl. $R_5$ and $R_6$ may be linked to form an aromatic ring, for example a phenyl ring, as shown in structure 1a below.

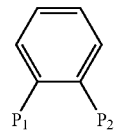

Structure (1a)

1,2 phenylene backbone

Ligands of general structures 2 and 3 will form rigid six and seven membered rings respectively. In particular, it is believed that rotation of the ligand of structure 3 about the single bridge bond is prevented by the steric hindrance of overlapping hydrogen atoms in the structure.

Suitably, the structures 1, 1a, 2 and 3 above may be substituted by one or more substituents, such as by one or more alkyl groups, including substitution of the P1 and/or P2 groups.

In particular, $R^1$, $R^2$, $R^3$ and $R^4$ of the P1 and P2 groups present in structures 1, 1a, 2 and 3 above are preferably each independently selected from phenyl groups and substituted phenyl groups. More preferably one or more of the $R^1$, $R^2$, $R^3$ and $R^4$ groups are substituted, preferably at one or more of the ortho positions. Preferred ortho-substituents include alkyl, aryl or alkyloxy (OR) groups. Particularly preferred ortho-substituents are Me, $CF_3$, Et, iso-Pr and OMe.

To improve the solubility of the bidentate ligands represented by the structures 1, 1a, 2 and 3 above, and thus the catalyst in the liquid reaction composition, the bidentate ligands may be substituted with one or more hydrophilic and/or polar groups. Preferably one or more of the phosphorous-containing groups of the bidentate ligand is substituted. Examples of suitable substituents include —$CO_2H$, —$CO_2Me$, —OH, —$SO_3H$, —$SO_3Na$, —$NH_2$, —$NH_3^+$ and —$NR_2H^+$.

Preferred bidentate arsine and stibine ligands may be represented by structures 1, 1a, 2 and 3 above, or variants thereof as described, and wherein the phosphorus atoms are replaced by arsenic or antimony atoms. Preferred mixed bidentate ligands include structures 1, 1a, 2 and 3 above, or variants thereof as described, and which comprise a combination of two groups selected from phosphorus, arsenic and antimony-containing groups.

Preferred bidentate nitrogen-containing ligands are aromatic ring systems which contain nitrogen as the donor atom. The aromatic rings may be either substituted or unsubstituted and the ring system may also comprise other heteroatoms such as oxygen. Examples of suitable ring systems include substituted and unsubstituted bipyridines.

The polydentate ligand of the present invention may also be a tridentate ligand.

The tridentate ligand has three coordinating groups through which the ligand coordinates to the rhodium or iridium metal centre. The three coordinating groups may be represented by L1 and L2, as defined previously, and L3, a third coordinating group, which preferably contains P, As, Sb, O, N, S or carbene as the donor (co-ordinating) atom.

Preferably the tridentate ligand is represented by the formula L1($R^7$)L3($R^8$)L2, wherein $R^7$ and $R^8$ are linking groups that link L1 to L3 and L3 to L2 respectively. The linking groups $R^7$ and $R^8$ are independently selected from aryl and alkenyl groups, preferably vinylic or phenyl groups. $R^7$ and $R^8$ may themselves form at least one cyclic structure comprising L3, which may be represented by the generic structure A below:

Structure A

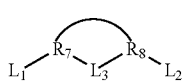

Preferably, the tridentate ligand is represented by the formula L1($R^7$)L3($R^8$)L2 as described above, and coordinates to the rhodium or iridium catalyst metal centre in a bridging conformation, such that L1 and L2 are mutually trans with respect to the metal centre. By mutually trans, as used throughout this specification, is meant that the angle formed by the two ligands and the metal centre, L1-M-L2, wherein M is the Rh or Ir metal centre, is at least 145°, preferably at least 150°. The angle may be measured using conventional techniques, such as X-ray crystallography.

Preferably, the tridentate ligand co-ordinates such that the donor atoms in the L1, L2 and L3 groups are in a meridional (mer-) co-ordination mode with respect to the metal centre. More preferably, the tridentate ligand co-ordinates such that the donor atoms of the L1, L2 and L3 groups are in an essentially planar configuration with respect to the metal centre.

Preferably, L1 and L2 are phosphorous-containing groups and L3 is oxygen, such that the tridentate ligand has the formula P1-$R^7$—O—$R^8$-P2, wherein P1 and P2 are phosphine-containing groups of general formula $R^1R^2P$ and $R^3R^4P$, and wherein $R^1$, $R^2$, $R^3$ and $R^4$ are each independently selected from unsubstituted or substituted alkenyl groups, alkyl groups, aryl groups, especially phenyl groups. Preferably, $R^1$, $R^2$, $R^3$ and $R^4$ in the tridentate ligand are each a phenyl group. Each of the phenyl groups may be substituted or unsubstituted. Each of P1 and P2 may be diphenylphosphine ($PPh_2$). Alternatively, one or more of the $R^1$, $R^2$, $R^3$ and $R^4$ phenyl groups in the P1 and P2 groups are substituted. Suitably the phenyl groups may be substituted at one or more of the ortho positions by at least one group selected from alkyl, aryl or alkyloxy (OR) groups. Particularly preferred ortho substituents are Me, $CF_3$, Et, iso-Pr and OMe.

To improve the solubility of the tridentate ligand, and hence the catalyst, in the liquid reaction composition one or more of the $R^1$, $R^2$, $R^3$, $R^4$, $R^7$ and $R^8$ groups on the tridentate ligand may be substituted with one or more hydrophilic and/or polar groups. Examples of suitable substituents include —$CO_2H$, —$CO_2Me$, —OH, —$SO_3H$, —$SO_3Na$, —$NH_2$, —$NH_3^+$ and —$NR_2H^+$.

The rigid conformation of the tridentate metal-ligand complex may be the direct result of the ligand structure or may be a result of the structure of the metal ligand complex. For example, the rigid conformation may be the result of a rigid structure of the overall ligand, such as Xantphos (structure 4 below). Thus, the tridentate Xantphos ligand, when complexed with the rhodium or iridium metal centre (atom), forms a rigid ring structure comprising the metal atom, the coordinating P, As or Sb atoms and the ligand backbone (having oxygen as the third donor).

Alternatively, the rigid conformation may be the result of $R^7$ and $R^8$ each being, independently, a vinylic or an aromatic backbone, which hinder or prevent rotation of the ligand backbone between L1 and L3, and between L3 and L2 respectively, but where the overall ligand is rigid only when coordinated to a metal centre;. An example of such a structure is DPEphos, which is shown as structure 5 below. In this example, the ligand, when coordinated to the rhodium or iridium metal centre, forms a rigid ring structure comprising two rigid five-membered rings that give an overall rigidity to the ligand-metal complex. Alternatively, or additionally, the ligand-metal complex may be rigid due to steric effects that hinder rotation of the ligand backbone, as described previously for structure 3.

Specific examples of suitable tridentate phosphine-containing ligands for use in the present invention include Xantphos, Thixantphos, Sixantphos, Homoxantphos, Phosxantphos, Isopropxantphos, Nixantphos, Benzoxantphos, DPEphos, DBFphos and R-Nixantphos, having structures 4-14 which are given below. The R grouping of R-Nixantphos is preferably selected from alkyl and aryl groups, and more preferably selected from methyl, ethyl, propyl and benzyl.

4. Xantphos

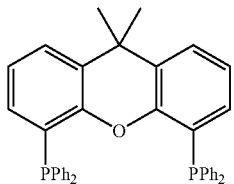

5. DPEphos

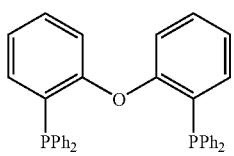

6. Sixantphos

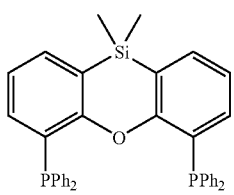

7. Homoxantphos

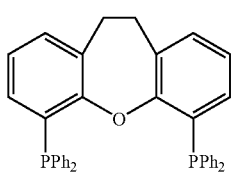

8. Phosxantphos

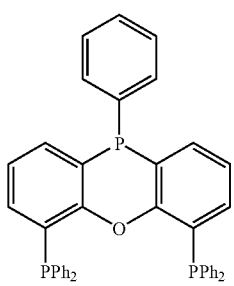

9. Isopropxantphos

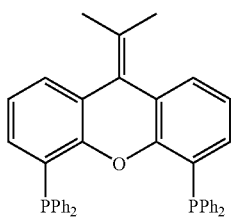

10. Nixantphos

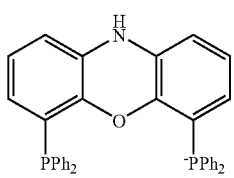

11. R-Nixantphos

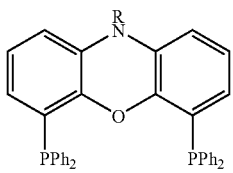

12. Benzoxantphos

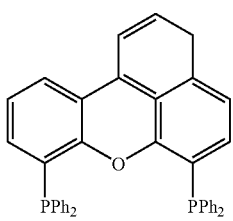

13. Thixantphos

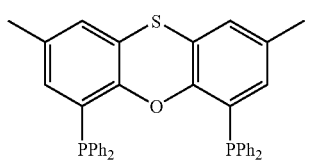

14. DBFphos

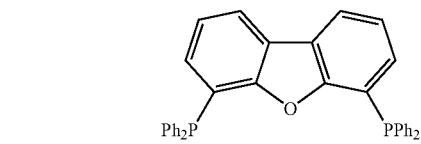

Suitably, structures 4 to 14 above, may be substituted by one or more substituents, such as one or more alkyl groups, for example. The structure of t-Bu-xantphos is shown as structure 15 below.

Structure 15

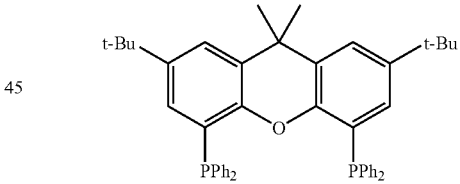

In the tridentate phosphine-containing ligands represented by structures 4 to 15, the diphenylphosphine groups may be replaced by P1 and P2 groups as previously defied. In particular, preferred P1 and P2 groups are $R^1R^2P$ and $R^3R^4P$ groups wherein $R^1$, $R^2$, $R^3$ and $R^4$ are each, independently selected from phenyl groups and substituted phenyl groups and one or more of the $R^1$, $R^2$, $R^3$ and $R^4$ groups are substituted, preferably at one or more of the ortho positions, with alkyl, aryl or alkyloxy (OR) groups. Particularly preferred ortho-substituents are Me, $CF_3$, Et, iso-Pr and OMe.

To improve the solubility of the tridentate ligands represented by structures 4 to 15, and thus the catalyst, in the liquid reaction composition, the tridentate ligands may be substituted with one or more hydrophilic and/or polar groups, especially on one or more of the phosphine groups on the tridentate ligand. Examples of suitable substituents include —CO₂H, —CO₂Me, —OH, —SO₃H, —SO₃Na, —NH₂, —NH₃⁺ and —NR₂H⁺.

Suitably, the tridentate phosphine containing ligands of any of the above structures 4 to 15, or substituted variants thereof as described above, may have the oxygen atom in L3 substituted by a sulphur atom or a nitrogen atom.

Preferred tridentate arsine- and stibine-containing ligands include structures 4 to 15 above, or variants thereof as described herein, wherein the phosphorus atoms are replaced by arsenic or antimony atoms. Preferred mixed tridentate ligands include structures 4 to 15 above, or variants thereof as described herein, comprising, as L1 and L2, a combination of two groups selected from phosphorus, arsenic and antimony-containing groups.

For example, the structures of As, As-t-Bu-xantphos and P, As-t-Bu-xantphos are given below as structures 16 and 17 respectively.

Structure 16

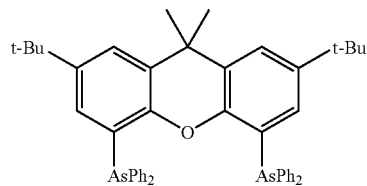

Structure 17

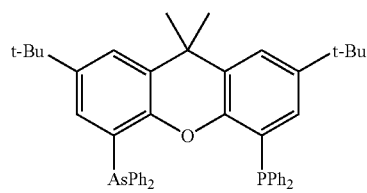

Preferred tridentate nitrogen-containing ligands are aromatic ring systems which contain nitrogen as the donor atom. The aromatic rings may be either substituted or unsubstituted and the ring system may also comprise other heteroatoms such as oxygen. Examples of suitable ring systems include substituted and unsubstituted terpyridines.

The bidentate and tridentate ligands are either commercially available or may be synthesised according to methods known in the art. More specifically, the tridentate ligands represented by structures 4 to 17, and variants thereof as described, may be synthesised according to methods as described or analogous to those described by van der Veen et al., Chem. Commun., 2000, 333, the contents of which are herein incorporated by reference.

The use of a catalyst that comprises rhodium or iridium coordinated with a polydentate ligand in a rigid structural conformation or which has a bite angle of at least 145° according to the present invention has been found to give improved selectivity to carboxylic acid products and reduced selectivity to liquid hydrogenation by-products, such as alcohols and aldehydes, in the presence of hydrogen.

Preferably, the catalyst of the present invention comprises rhodium. The proposed mechanisms of rhodium catalysed carbonylation and reductive carbonylation can be found, for example, in Moloy et al., Organometallics, Vol. 8, No. 12, 1989, the contents of which are herein incorporated by reference. Without wishing to be bound by theory it is believed that the rigid conformation of the metal-ligand complexes according to the present invention prevents or at least inhibits the ability of the metal-ligand complex to change conformation, which in turn prevents or at least inhibits hydrogen addition to the metal-ligand complex or prevents the elimination of an aldehyde (e.g. acetaldehyde) from a metal acyl species (e.g. M-COCH₃) formed during carbonylation, such an elimination reaction requiring either H₂ to enter a vacant site cis to the acyl group or a reductive elimination reaction between a metal hydride ligand (formed via H₂ addition) and metal acyl ligand which are mutually cis. For example, in the case of a metal complex with a square pyramid structure containing a rigid bidentate ligand with an apical acyl group (e.g. COMe) and two halide ligands (e.g. I) the vacant site is fixed in a position trans to the acyl group, thereby preventing its reaction with hydrogen to form an aldehyde.

In addition, and again without wishing to be bound by theory, it is also believed that the tridentate ligands, by coordinating with three donors, may have an additional steric blocking effect that prevents or inhibits hydrogen addition to the metal-ligand complex.

The catalyst of the present invention may be prepared by coordinating an iridium- or rhodium-containing compound with a polydentate ligand. The catalyst may be formed in situ in the liquid reaction composition, by the separate addition of an iridium- or rhodium-containing compound and a polydentate ligand to the liquid reaction composition. The iridium- or rhodium-containing compound may be added in any suitable form which dissolves in the liquid reaction composition or is convertible to a soluble form. Preferably, however, the catalyst is added to the liquid reaction composition in the form of a pre-formed metal-polydentate ligand complex in which the polydentate ligand is coordinated to the iridium- or rhodium-containing compound. The pre-formed metal-polydentate ligand complex may be prepared, for example, by mixing a suitable iridium- or rhodium-containing compound having displaceable groups with the polydentate ligand in a suitable solvent, for example methanol, prior to addition to the liquid reaction composition.

Examples of pre-formed iridium-tridentate ligand complexes include [{L1(R⁷)L3(R⁸)L2}Ir(COMe)I₂], [{L1(R⁷)L3(R⁸)L2}Ir(CO)I], [{L1(R⁷)L3(R⁸)L2}Ir(CO)]⁺ and [{L1(R⁷)L3(R⁸)L2}IrI(CO)Me]⁺, wherein L1(R⁷)L3(R⁸)L2 represents the tridentate ligand as hereinbefore described.

Examples of pre-formed rhodium-tridentate ligand complexes include [{L1(R⁷)L3(R⁸)L2}Rh(COMe)I₂], [{L1(R⁷)L3(R⁸)L}Rh(CO)I], [{L1(R⁷)L3(R⁸)L2}Rh(CO)]⁺ and [{L1(R⁷)L3(R⁸)L2}RhI(CO)Me]⁺, wherein L1(R⁷)L3(R⁸)L2 represents the tridentate ligand as previously described, for example [{Xantphos}Rh(COMe)I₂].

Preferably the iridium- or rhodium-containing compound is a chloride free compound, such as an acetate, which is soluble in one or more of the liquid reaction composition components, and so may be added to the reaction as a solution therein.

Examples of suitable iridium-containing compounds include IrCl₃, IrI₃, IrBr₃, [Ir(CO)₂I]₂, [Ir(CO)₂Cl]₂, [Ir(CO)₂Br]₂, [Ir(CO)₄I₂]⁻H⁺, [Ir(CO)₂Br₂]⁻H⁺, [Ir(CO)₂I₂]⁻H⁺, [Ir(CH₃)I₃(CO)₂]⁻H⁺, Ir₄(CO)₁₂, IrCl₃.4H₂O, IrBr₃.4H₂O, Ir₃(CO)₁₂, iridium metal, Ir₂O₃, IrO₂, Ir(acac)(CO)₂, Ir(acac)₃, iridium acetate, [Ir₃O(OAc)₆(H₂O)₃][OAc], and hexachloroiridic acid H₂[IrCl₆], preferably, chloride-free complexes of iridium such as acetates, oxalates and acetoacetates.

Examples of suitable rhodium-containing compounds include [Rh(CO)₂Cl]₂, [Rh(CO)₂I]₂, [Rh(Cod)Cl]₂, rhodium (III) chloride, rhodium (III) chloride trihydrate, rhodium (III) bromide, rhodium (III) iodide, rhodium (III) acetate, rhodium dicarbonylacetylacetonate, RhCl(PPh$_3$)$_3$ and RhCl(CO)(PPh$_3$)$_2$.

Preferably, the concentration of iridium in the liquid reaction composition is in the range 100 to 6000 ppm by weight of iridium, more preferably in the range 400 to 5000 ppm, such as in the range 500 to 3000 ppm by weight.

Preferably, the concentration of rhodium in the liquid reaction composition is in the range 25 to 5000 ppm by weight of rhodium, more preferably, in the range 250 to 3500 ppm.

The mole ratio of the rhodium or iridium metal to the polydentate ligand in the reactor is optimally approximately 1:1, especially where a pre-formed metal-ligand complex is employed. Alternatively, an excess of ligand may be present in the liquid reaction composition, especially, for example, where the metal-ligand complex is to be formed in-situ. Thus, the mole ratio of the rhodium or iridium metal to the polydentate ligand may be less than 1:1, suitably be in the range from 1:1 to 1:2.

The liquid reaction composition may also comprise a promoter metal. Suitable promoters are selected from ruthenium, osmium, rhenium, cadmium, mercury, zinc, gallium, indium and tungsten. Preferred promoters are selected from ruthenium and osmium, most preferably, ruthenium. The promoter may comprise any suitable promoter metal-containing compound which is soluble in the liquid reaction composition. The promoter may be added to the liquid reaction composition for the carbonylation reaction in any suitable form which dissolves in the liquid reaction composition or is convertible to soluble form.

Examples of suitable ruthenium-containing compounds which may be used as sources of promoter include ruthenium (III) chloride, ruthenium (III) chloride trihydrate, ruthenium (III) chloride, ruthenium (III) bromide, ruthenium metal, ruthenium oxides, ruthenium (III) formate, [Ru(CO)$_3$I$_3$]$^-$H+, [Ru(CO)$_2$I$_2$]$_n$, [Ru(CO)$_4$I$_2$], [Ru(CO)$_3$I$_2$]$_2$, tetra(aceto)chlororuthenium(II,III), ruthenium (III) acetate, ruthenium (III) propionate, ruthenium (III) butyrate, ruthenium pentacarbonyl, trirutheniumdodecacarbonyl and mixed ruthenium halocarbonyls such as dichlorotricarbonylruthenium (II) dimer, dibromotricarbonylruthenium (II) dimer, and other organoruthenium complexes such as tetrachlorobis (4-cymene)diruthenium(II), tetrachlorobis(benzene)diruthenium(II), dichloro(cycloocta-1,5diene) ruthenium (II) polymer and tris(acetylacetonate)ruthenium (III).

Examples of suitable osmium-containing compounds which may be used as sources of promoter include osmium (III) chloride hydrate and anhydrous, osmium metal, osmium tetraoxide, triosmiumdodecacarbonyl, [Os(CO)$_4$I$_2$], [Os(CO)$_3$I$_2$]$_2$, [Os(CO)$_3$I$_3$]$^-$H+, pentachloro-µ-nitrodiosmium and mixed osmium halocarbonyls such as tricarbonyldichloroosmium (II) dimer and other organoosmium complexes.

Examples of suitable rhenium-containing compounds which may be used as sources of promoter include Re$_2$(CO)$_{10}$, Re(CO)$_5$Cl, Re(CO)$_5$Br, Re(CO)$_5$I, ReCl$_3$.xH$_2$O, [Re(CO)$_4$I]$_2$, Re(CO)$_4$I$_2$]$^-$H$^+$ and ReCl$_5$.yH$_2$O.

Examples of suitable cadmium-containing compounds which may be used include Cd(OAc)$_2$, CdI$_2$, CdBr$_2$, CdCl$_2$, Cd(OH)$_2$, and cadmium acetylacetonate.

Examples of suitable mercury-containing compounds which may be used include Hg(OAc)$_2$, HgI$_2$, HgBr$_2$, HgCl$_2$, Hg$_2$I$_2$, and Hg$_2$Cl$_2$.

Examples of suitable zinc-containing compounds which may be used include Zn(OAc)$_2$, Zn(OH)$_2$, ZnI$_2$, ZnBr$_2$, ZnCl$_2$, and zinc acetylacetonate.

Examples of suitable gallium-containing compounds which may be used include gallium acetylacetonate, gallium acetate, GaCl$_3$, GaBr$_3$, GaI$_3$, Ga$_2$Cl$_4$ and Ga(OH)$_3$.

Examples of suitable indium-containing compounds which may be used include indium acetylacetonate, indium acetate, InCl$_3$, InBr$_3$, InI$_3$ and In(OH)$_3$.

Examples of suitable tungsten-containing compounds which may be used include W(CO)$_6$, WCl$_4$, WCl$_6$, WBr$_5$, WI$_2$, C$_9$H$_{12}$W(CO)$_3$ and any tungsten chloro-, bromo-, or iodo-carbonyl compound.

Preferably, the promoter is present in an effective amount up to the limit of its solubility in the liquid reaction composition and/or any liquid process streams recycled to the carbonylation reactor from the carboxylic acid recovery stage. The promoter is suitably present in the liquid reaction composition at a molar ratio of promoter to rhodium or iridium of 0.1:1 to 20:1, preferably 0.5:1 to 10:1, more preferably 2:1 to 10:1. A suitable promoter concentration is less than 8000 ppm, such as 400 to 7000 ppm.

The liquid reaction composition may also comprise an effective amount of a stabiliser and/or promoter compound selected from alkali metal iodides, alkaline earth metal iodides, metal complexes capable of generating I—, salts capable of generating I—, and mixtures of two or more thereof. Examples of suitable alkali metal iodides include lithium iodide, sodium iodide and potassium iodide, preferably lithium iodide. Suitable alkaline earth metal iodides include calcium iodide. Suitable metal complexes capable of generating I— include complexes of the lanthanide metals, for example, samarium and gadolinium, cerium, and other metals such as molybdenum, nickel, iron, aluminium and chromium. Salts capable of generating I— include, for example, acetates which are capable of conversion in-situ to I— typically LiOAc and organic salts, such as quaternary ammonium iodides and phosphonium iodides, which may be added as such.

Suitably, the amount of stabilising compound used is such that it is effective in providing an increase in the solubility of the catalyst system and preferably, does not significantly decrease the carbonylation reaction rate.

Corrosion metals, such as chromium, iron and molybdenum, which may have an adverse affect on the reaction rate, may be minimised by using suitable corrosion resistant materials of construction. Corrosion metal and other ionic impurities may be reduced by the use of a suitable ion exchange resin bed to treat the liquid reaction composition, or preferably a catalyst recycle stream. Such a process is described in U.S. Pat. No. 4,007,130.

The alkyl halide co-catalyst may suitably be a lower, e.g. C$_1$ to C$_4$, alkyl halide. Preferably the alkyl halide is an alkyl iodide, such as methyl iodide. The concentration of alkyl halide co-catalyst in the liquid reaction composition is suitably in the range of from 1 to 30% by weight, for example from 1 to 20% by weight.

In the process of the present invention, a reactant chosen from an alcohol and/or a reactive derivative thereof is carbonylated with carbon monoxide to produce a carboxylic acid and/or the alcohol ester of a carboxylic acid.

A suitable alcohol reactant is any alcohol having from 1 to 20 carbon atoms and at least one hydroxyl group. Preferably the alcohol is a monofunctional aliphatic alcohol, preferably having from 1 to 8 carbon atoms. Most preferably the alcohol is methanol, ethanol and/or propanol. A mixture comprising more than one alcohol may be used. The carbonylation product of the alcohol will be a carboxylic acid having one carbon atom more than the alcohol and/or an ester of the alcohol and the carboxylic acid product. A particularly preferred reactant is methanol, the carbonylation product of which is acetic acid and/or methyl acetate.

Suitable reactive derivatives of an alcohol include esters, halides and ethers.

A suitable ester reactant is any ester of an alcohol and a carboxylic acid. Preferably the ester reactant is an ester of a carboxylic acid and an alcohol which alcohol has from 1 to 20 carbon atoms. More preferably the ester reactant is an ester of a carboxylic acid and a monofunctional aliphatic alcohol which alcohol has from 1 to 8 carbon atoms. Most preferably the ester reactant is an ester of a carboxylic acid and methanol, ethanol or propanol. Preferably the ester reactant is an ester of an alcohol and the carboxylic acid product. Preferably the ester reactant has up to 20 carbon atoms. A mixture of ester reactants may be used. The carboxylic acid carbonylation product of the ester reactant will be a carboxylic acid having one carbon atom more than the alcohol component of the ester reactant. A particularly preferred ester reactant is methyl acetate, the carbonylation product of which is acetic acid.

A suitable halide reactant is any hydrocarbyl halide having up to 20 carbon atoms. Preferably the halide reactant is an iodide or a bromide. More preferably the halide component of the hydrocarbyl halide reactant is the same halide as that of the alkyl halide co-catalyst. Most preferably the hydrocarbyl halide is a hydrocarbyl iodide, most preferably methyl iodide, ethyl iodide or propyl iodide. A mixture of hydrocarbyl halide reactants may be used. The carboxylic acid product of the hydrocarbyl halide reactant will be a carboxylic acid having one more carbon atom than the hydrocarbyl halide reactant. The ester carbonylation product of the hydrocarbyl halide will be the ester of the hydrocarbyl halide and a carboxylic acid having one more carbon atom than the hydrocarbyl halide.

A suitable ether reactant is any hydrocarbyl ether having up to 20 carbon atoms. Preferably the ether reactant is a dialkyl ether, most preferably dimethyl ether, diethyl ether or dipropyl ether. A mixture of ethers may be used. The carbonylation products of the ether reactant will be carboxylic acids having one carbon atom more than each of the hydrocarbyl groups of the ether, and/or ester derivatives thereof. A particularly preferred ether reactant is dimethyl ether, the carboxylic acid product of which is acetic acid.

A mixture of alcohol, ester, halide and ether reactants may be used in the carbonylation process. More than one alcohol, ester, halide and/or ether may be used. A particularly preferred reactant is methanol and/or methyl acetate, the carboxylic acid carbonylation products of which are acetic acid.

The liquid reaction composition may be anhydrous but preferably comprises a finite concentration of water. By anhydrous as used herein is meant that the liquid reaction composition is essentially free of water, such that the liquid reaction composition comprises less than 0.1 wt % water. By finite concentration of water, as used herein, meant that the liquid reaction composition comprises at least 0.1 wt % water. Preferably, water may be present at a concentration in the range from 0.1 to 30%, for example from 1 to 15%, and more preferably from 1 to 10%, by weight based on the total weight of the liquid reaction composition.

Water may be added to the liquid reaction composition, where desired, or may be formed in situ in the carbonylation reaction. For example, in the carbonylation of methanol, water may be formed by the esterification reaction between methanol reactant and acetic acid product.

The water may be introduced to the carbonylation reactor together with or separately from the other reactants such as esters, for example methyl acetate. Water may be separated from the liquid reaction composition withdrawn from the reactor and recycled in controlled amounts to maintain the required concentration in the liquid reaction composition.

The carboxylic acid product, for example, acetic acid may be present as a solvent in the liquid reaction composition of the present invention.

The carbon monoxide for use in the present invention (when fed separately to a hydrogen feed) may be essentially pure or may contain inert impurities such as carbon dioxide, methane, nitrogen, noble gases, water and $C_1$ to $C_4$ paraffinic hydrocarbons.

The partial pressure of carbon monoxide in the reactor may suitably be in the range from 1 to 70 barg.

Hydrogen may be fed to the reactor separately from the carbon monoxide feed, but is preferably fed to the reactor as a mixture with carbon monoxide. Preferably, a mixture of carbon monoxide and hydrogen is obtained from a commercial source such as from the reforming of hydrocarbons. The commercial reforming of hydrocarbons produces a mixture of CO, hydrogen and $CO_2$, such mixture being generally referred to as syngas. Syngas typically comprises a mol ratio of hydrogen to CO in the range 1.5:1 to 5:1.

The mixed hydrogen/carbon monoxide feed may contain at least 1 mol % hydrogen, such as at least 2 mol % hydrogen and, more preferably, at least 5 mol % hydrogen. The hydrogen to CO mole ratio in the feed is most preferably between 1:100 and 10:1, such as 1:20 to 5:1.

Where hydrogen is fed to the reactor with CO, the CO consumption in the reactor causes the molar ratio of hydrogen to CO in the reactor to be generally higher than the molar ratio of hydrogen to CO in the feed to the reactor. In addition to hydrogen fed to the reaction, hydrogen also may be produced in-situ by the water-gas shift reaction. Thus, where hydrogen is present in the feed to the reactor, and particularly for a carbonylation process operated at high CO conversion, such as a batch process, the level of CO in the reactor may become quite low, and the molar ratio of hydrogen to CO in the reactor may get correspondingly high, such as 100:1 or higher. Preferably, however, the hydrogen to CO molar ratio in the reactor is maintained at less than 100:1. Preferably, there is maintained in the carbonylation reactor, hydrogen at a hydrogen:CO mole ratio of at least 1:100. More preferably there is maintained in the carbonylation reactor, hydrogen at a hydrogen:CO mole ratio of at least 1:10, most preferably at least 1:1. The hydrogen partial pressure in the reactor is preferably greater than 1 bar, most preferably greater than 2 bar.

The carbonylation reaction may be carried out at a total pressure in the range from 10 to 100 barg. The temperature may suitably be in the range from 50 to 250° C., typically from 120 to 200° C.

The process may be operated batchwise or continuously, preferably continuously.

The carboxylic acid product may be recovered from the liquid reaction composition by withdrawing vapour and/or liquid from the carbonylation reactor and recovering carboxylic acid from the withdrawn material. Preferably, carboxylic acid is recovered from the liquid reaction composition by continuously withdrawing liquid reaction composition from the carbonylation reactor and recovering carboxylic acid from the withdrawn liquid reaction composition by one or more flash and/or fractional distillation stages in which the acid is separated from the other components of the liquid reaction composition such as rhodium or iridium catalyst, alkyl halide co-catalyst, optional promoter, carboxylic acid ester, unreacted alcohol, water and carboxylic acid solvent which may be recycled to the reactor.

In a conventional process for the production of a carboxylic acid, a purge is usually taken to keep the hydrogen at low partial pressure in the reactor (the hydrogen builds up due to impurity levels in the carbon monoxide feed and hydrogen formed in situ). Since only low levels of hydrogen can be tolerated, the purge often contains low levels of hydrogen and significant levels of carbon monoxide, which is disposed of. Since it has now been found that the process of the present invention can be operated with higher levels of hydrogen in the reactor, the purge stream will contain higher levels of hydrogen and so significantly less carbon monoxide need be purged from the reactor, thereby improving overall CO yield.

A further advantage of the process of the present invention is that high selectivity to the desired liquid products can be achieved in the presence of hydrogen, allowing carbon monoxide feed streams with higher contents of hydrogen to be employed in the carbonylation process. This has significant cost savings. In particular, utilising a carbon monoxide feed with greater than 1% $H_2$ allows less expensive, non-cryogenic, methods of syngas separation to be employed, such as membrane separation technologies.

The invention will now be illustrated by way of example only and with reference to the following examples:

EXAMPLES

General Reaction Method

Methanol, methyl iodide, $RuCl_3$.hydrate and dppp (dppp=bis-1,3-diphenylphosphinopropane) were obtained from Aldrich. The (acac)Rh(CO)$_2$, Xantphos and BINAP were obtained from Strem Chemicals. $RuCl_3$ was obtained from Johnson Matthey.

Experiments were performed using a 300 ml zirconium autoclave equipped with a magnetically driven stirrer with a gas dispersion impeller system, liquid catalyst injection facility and cooling coils. The gas supply to the autoclave was provided from a ballast vessel, feed gas being provided to maintain the autoclave at a constant pressure during reaction.

Comparative Example A

This experiment demonstrates the reaction of methanol with carbon monoxide in the presence of hydrogen, a rhodium catalyst, dppp and a ruthenium promoter during a 2 hour run time. Dppp is a bidentate phosphine ligand. Syngas comprising hydrogen and carbon at a $H_2$:CO mol ratio of 2:1 was used (no $CO_2$ was present in the syngas). 2.031 gram of (dppp)Rh(COMe)I$_2$ and 2.115 gram of $RuCl_3$ were suspended in a portion of the methanol charge and charged to the autoclave. The reactor was then pressure tested with nitrogen, vented via a gas sampling system, and flushed with synthesis gas three times. The remaining liquid components of the reaction composition (the remaining methanol and methyl iodide) were charged to the autoclave via a liquid addition port. The autoclave was then pressurised with 5 barg of syngas and slowly vented. The autoclave was then pressurised with synthesis gas (approximately 20 barg) and heated with stirring (1220 r.p.m.) to reaction temperature, 140° C. Once stable at temperature (about 15 minutes), the total pressure was raised to the desired operating pressure by feeding syngas from the ballast vessel. The reactor pressure was maintained at a constant value (±0.5 barg) by feeding gas from the ballast vessel throughout the experiment. Gas uptake from the ballast vessel was measured using datalogging facilities throughout the course of the experiment. The reaction temperature was maintained within ±1° C. of the desired reaction temperature by means of a heating mantle connected to a Eurotherm (Trade Mark) control system. After a suitable time, T, (see Table 1b), the ballast vessel was isolated and the reactor rapidly cooled by use of the cooling coils.

Product distribution data is given in Table 2, product selectivity data is given in Table 3. The predominating liquid products are ethanol and its derivatives (EtOMe and Et$_2$O) plus its precursor acetaldehyde. Acetic acid and its derivative MeOAc are formed in relatively small amounts.

Comparative Example B

This experiment demonstrates the reaction of methanol with carbon monoxide in the presence of hydrogen, a rhodium catalyst, dppp and a ruthenium promoter during a 30 min run time. Syngas comprising hydrogen and carbon at a $H_2$:CO mol ratio of 2:1 was used (no $CO_2$ was present in the syngas).

In this experiment the phosphine-rhodium complex was generated in situ. 1.114 gram of dppp was placed in a portion of the methanol charge (ca. 60 g) with 0.658 gram of (acac)Rh(CO)$_2$ to form a catalyst precursor suspension. 2.590 gram of $RuCl_3.3H_2O$ was placed in the autoclave together with approximately 5 gram of methanol and the autoclave was pressure tested. The MeI co-catalyst was added to the autoclave followed by the catalyst precursor suspension. The remaining methanol was added and the autoclave was pressurised with syngas (approximately 20 barg). The experiment was then conducted as for Comparative Example A. Reaction conditions are given in Table 1b. Product distribution data is given in Table 2, product selectivity data is given in Table 3. The predominant liquid products are ethanol plus its precursor acetaldehyde. Acetic acid and its derivative MeOAc are formed in relatively small amounts.

Comparative Example C

This experiment demonstrates the reaction of methanol with carbon monoxide in the presence of hydrogen, a rhodium catalyst, dppp, but in the absence of a ruthenium promoter, during a 2 hour run time. Syngas comprising hydrogen and carbon at a $H_2$:CO mol ratio of 2:1 was used (no $CO_2$ was present in the syngas).

The reaction was performed according to the method of Comparative Example B using a charge composition and reaction conditions as shown in Tables 1a and 1b below. Product distribution data is given in Table 2. Product selectivity data is given in Table 3. In the absence of ruthenium the main liquid product is acetaldehyde. Acetic acid and its derivative MeOAc are also formed.

Example 1

This example demonstrates the reaction of methanol with carbon monoxide in the presence of hydrogen, a rhodium Xantphos based catalyst and a ruthenium promoter. Syngas comprising hydrogen and carbon at a $H_2$:CO mol ratio of 2:1 was used (no $CO_2$ was present in the syngas).

In this experiment the phosphine-rhodium complex was generated in situ. 1.571 gram of Xantphos was placed in a portion of the methanol charge (ca. 60 g) with 0.646 gram of (acac)Rh(CO)$_2$ and 2.084 gram of RuCl$_3$ to form a catalyst precursor suspension. The MeI co-catalyst was added to the catalyst injection system along with a small amount of methanol (5 gram). The catalyst precursor suspension was added to the autoclave, followed by the remaining methanol and the autoclave was pressurised with syngas (approximately 20 barg). The experiment was then conducted as for Comparative Example A, using a charge composition and reaction conditions as given in Tables 1a and 1b below. Product distribution data is given is Table 2. Product selectivity data is given in Table 3.

Example 2

This example demonstrates the reaction of methanol with carbon monoxide in the presence of hydrogen, a rhodium Xantphos based catalyst, and in the absence of a ruthenium promoter. Syngas comprising hydrogen and carbon at a $H_2$:CO mol ratio of 2:1 was used (no $CO_2$ was present in the syngas).

The reaction was performed according to the method of Comparative Example C using a charge composition and reaction conditions as given in Tables 1a and 1b below. Product distribution data is given is Table 2. Product selectivity data is given in Table 3.

Examples 3 to 13

Examples 3 to 11 were conducted according to the method of Comparative Example B using charge compositions and reaction conditions as shown in Tables 1a and 1b. Product distribution data is given is Table 2. Product selectivity data is given in Table 3.

The structures of the ligands of Examples 3-4 and 6-13 are as follows:

TABLE 1b

Reaction conditions and gas uptake during the reaction.

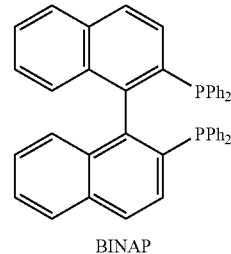

BINAP

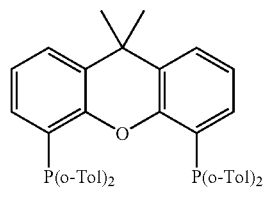

o-Tol-Xantphos

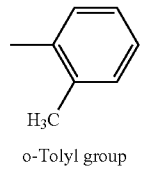

o-Tolyl group

TABLE 1a

Charge compositions for rhodium catalysed reactions in a 300 ml zirconium batch autoclave.

| Example | Ligand | Ligand (g) | Complex (g) | (acac)Rh(CO)$_2$ (g) | RuCl$_3$ (g) | MeOH (g) | MeI (g) |
|---|---|---|---|---|---|---|---|
| A | | | 2.031 | 0 | 2.115 | 80.05 | 14.50 |
| B | Dppp | 1.114 | | 0.658 | 2.590(*) | 79.35 | 14.36 |
| C | Dppp | 1.215 | | 0.637 | 0 | 79.75 | 14.58 |
| 1 | Xantphos | 1.571 | | 0.646 | 2.084 | 79.48 | 14.58 |
| 2 | Xantphos | 1.571 | | 0.651 | 0 | 78.47 | 14.49 |
| 3 | BINAP | 1.692 | | 0.651 | 2.032 | 79.62 | 14.40 |
| 4 | oTol-Xantphos | 0.711 | | 0.267 | 0.860 | 79.42 | 14.87 |
| 5 | Nixantphos | 0.749 | | 0.318 | 1.079 | 79.37 | 7.62 |
| 6 | Dpp-Benz | 1.215 | | 0.650 | 2.079 | 79.99 | 10.13 |
| 7 | TRIPHOS | 1.468 | | 0.659 | 2.102 | 80.85 | 14.46 |
| 8 | BIPHEP | 1.436 | | 0.646 | 2.114 | 80.02 | 14.53 |
| 9 | TERPHOS | 1.742 | | 0.656 | 2.135 | 79.36 | 14.46 |
| 10 | PNP-Phos | 1.136 | | 0.606 | 1.975 | 81.15 | 15.07 |
| 11 | TERPY | 0.662 | | 0.659 | 2.112 | 79.89 | 14.65 |
| 12 | BISBI | 1.153 | | 0.652 | 2.109 | 79.90 | 14.46 |
| 13 | Dpp-eae | 1.519 | | 0.512 | 1.684 | 80.26 | 14.32 |

(*)(H$_2$O)$_3$RuCl$_3$ used as the ruthenium source.

TABLE 1b-continued

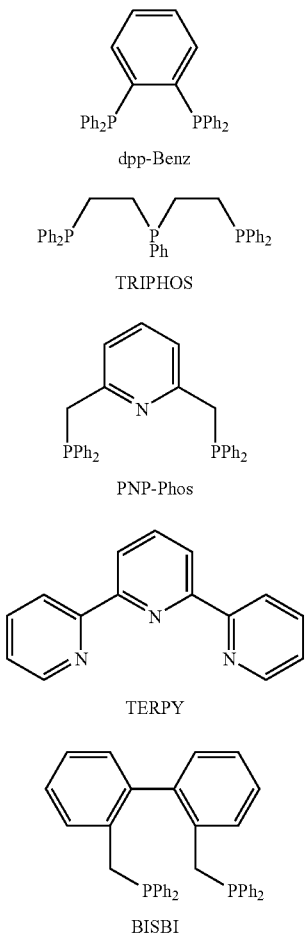

dpp-Benz

TRIPHOS

PNP-Phos

TERPY

BISBI

TABLE 1b-continued

Dpp-eae

| Example | Reaction temperature T(° C.) | Reaction pressure P(bar) | Reaction Time/ mins | Pressure drop (bar) |
|---|---|---|---|---|
| A | 140 | 67 | 120 | 61.8 |
| B | 140 | 67 | 30 | 13.4 (26.8*) |
| C | 140 | 70 | 120 | 17.9 |
| 1 | 140 | 68.7 | 17 | 5.8 |
| 2 | 140 | 68.4 | 21 | 7.3 |
| 3 | 140 | 68.9 | 45 | 0.7 |
| 4 | 140 | 68 | 80 | 10.2 |
| 5 | 140 | 67 | 120 | 11.1 |
| 6 | 140 | 67 | 120 | 14.8 |
| 7 | 140 | 68 | 120 | 16.4 |
| 8 | 140 | 67.7 | 120 | 15.4 |
| 9 | 140 | 68 | 120 | 25.1 |
| 10 | 140 | 67 | 120 | 11.6 |
| 11 | 140 | 65.9 | 103 | 16.1 |
| 12 | 140 | 66.8 | 51 | 9.0 |
| 13 | 140 | 66.9 | 33 | 10.0 |

*Experiment in different autoclave with larger ballast vessel, recalculated gas uptake 26.8 bar may be compared to the other experiments

TABLE 2

Product Distribution.

| Example | MeOH | AcOH | MeOAc | EtOH | $Et_2O$ | EtOMe | $Me_2O$ | AcH |
|---|---|---|---|---|---|---|---|---|
| A | 28.6 | 1.1 | 4.5 | 14.2 | 0.4 | 3.5 | 8.2 | 0.9 |
| B | 54.0 | 0.3 | 3.7 | 5.3 | 0.1 | ND | 7.7 | 1.9 |
| C | 35.1 | 0.4 | 2.8 | <0.05 | 0.1 | <0.05 | 10.8 | 3.1 |
| 1 | 51.7 | 0.9 | 14.15 | 0.1 | 0.0 | 0.8 | 2.9 | 0.1 |
| 2 | 50.8 | 1.0 | 15.4 | 0.0 | 0.0 | 0.0 | 4.1 | 0.1 |
| 3 | 60.2 | 0.1 | 4.3 | 0.1 | 0.1 | 0.7 | 7.4 | 0.1 |
| 4 | 40.7 | 0.8 | 9.0 | 1.1 | 0.1 | ND | 9.7 | 0.4 |
| 5 | 48.5 | 1.1 | 13.1 | 1.3 | 0.1 | ND | 7.7 | 0.3 |
| 6 | 41.7 | 1.7 | 13.4 | 2.5 | 0.2 | ND | 8.4 | 0.1 |
| 7 | 34.4 | 2.0 | 11.2 | 2.1 | 0.1 | ND | 10.0 | 0.7 |
| 8 | 35.9 | 1.6 | 10.6 | 1.9 | 0.3 | ND | 8.9 | 1.0 |
| 9 | 41.6 | 0.8 | 7.2 | 6.0 | 0.2 | ND | 9.4 | 0.4 |
| 10 | 44.7 | 0.5 | 5.9 | 3.2 | 0.1 | ND | 12.4 | 0.2 |
| 11 | 32.9 | 1.6 | 9.3 | 3.2 | 0.1 | ND | 10.8 | 0.7 |
| 12 | 40.0 | 2.1 | 13.6 | 0.3 | 0.1 | ND | 7.4 | 0.3 |
| 13 | 39.8 | 1.3 | 11.9 | 0.6 | 0.1 | ND | 7.2 | 0.7 |

ND = none detected

TABLE 3

| Example | MeOH conversion %[a] | Sel. EtOH and Derivatives %[b] | Sel. AcOH and Derivatives %[c] | Sel. AcH %[d] | Sel. CH$_4$ % |
|---|---|---|---|---|---|
| A | 40.5 | 66.4 | 15.7 | 3.4 | 14.4 |
| B | 16.8 | 42.7 | 20.0 | 15.3 | 21.9 |
| C | 38.8 | 1.2 | 28.1 | 42.9 | 26.9 |
| 1 | 31.1 | 2.6 | 35.7 | 0.5 | 60.7 |
| 2 | 29.2 | 0 | 38.3 | 0.3 | 60.9 |
| 3 | 28.7 | 17.4 | 71.3 | 1.4 | 9.0 |
| 4 | 29 | 10.6 | 54.7 | 3.7 | 30.7 |
| 5 | 25 | 6.5 | 38.8 | 1.4 | 52.7 |
| 6 | 34 | 10.9 | 36.6 | 0.4 | 52.0 |
| 7 | 40 | 9.9 | 35.3 | 3.0 | 51.9 |
| 8 | 34 | 10.6 | 34.8 | 4.6 | 49.9 |
| 9 | 34 | 46.9 | 38.5 | 3.0 | 11.6 |
| 10 | 23 | 40.3 | 48.9 | 2.5 | 6.7 |
| 11 | 57 | 15.2 | 30.6 | 3.1 | 50.8 |
| 12 | 38 | 1.7 | 37.6 | 1.2 | 59.3 |
| 13 | 36 | 3.3 | 35.3 | 3.1 | 58.2 |

[a]Methanol conversion was calculated from the recovered methanol in the liquid product (Conversion % = 100 * (moles MeOH$_{init}$ − moles MeOH$_{recov}$)/moles MeOH$_{init}$). Typical mass balance is of the order of 80–90%, the main loss being that of volatile DME on venting the autoclave. For the purpose of calculation DME and the OMe groups in the compounds MeOEt, MeOAc and Dimethoxyethane are considered as unreacted methanol.
[b]The selectivity to ethanol and derivatives was based on the sum of the selectivity to EtOH and the ethyl groups in, Et$_2$O, MeOEt and EtOAc in the total liquid products recovered.
[c]The selectivity to acetic acid and derivatives was based on the sum of the selectivity to acetic acid and the acetate groups in AcOH, MeOAc and EtOAc in the total liquid products recovered.
[d]The selectivity acetaldehyde and derivatives was based on the sum of the selectivity to acetaldehyde and the ethylidene group in dimethoxyethane in the total liquid products recovered.
[e]The selectivity to methane was based on the amount of methane analysed in the autoclave headspace at the end of the reaction.

From an inspection of Tables 2 and 3 it can be clearly be seen that for Examples 1 to 11 using rigid metal-ligand catalysts and for Examples 12-13 using catalysts having a bite angle of at least 145° there is a substantial decrease in ethanol and ethanol derivatives compared to the results obtained for Comparative Examples A and B. Furthermore the main liquid carbonylation product is a mixture of acetic acid and methyl acetate.

In Examples 3 and 4 it can also be seen that there is a substantial reduction in methane formation for BINAP and o-tol-Xantphos containing catalysts compared to the Xantphos based catalysts of Examples 1 and 2.

The invention claimed is:

1. A process for the production of a carboxylic acid and/or the alcohol ester of a carboxylic acid, which process comprises carbonylating an alcohol and/or a reactive derivative of the alcohol which is selected from the group consisting of esters, halides, ethers and mixtures thereof, thereof with carbon monoxide in a liquid reaction composition in a carbonylation reactor, said liquid reaction composition comprising said alcohol and/or a reactive derivative thereof, a carbonylation catalyst and an alkyl halide co-catalyst and optionally a finite concentration of water, wherein said catalyst comprises at least one of rhodium or iridium which is coordinated with a polydentate ligand wherein said polydentate ligand has a bite angle of at least 145° or forms a rigid Rh or Ir metal-ligand complex and wherein said polydentate ligand comprises at least two coordinating groups which independently contain P, N, As or Sb as the coordinating atom of at least two of the co-ordinating groups and wherein in said process there is maintained hydrogen at a hydrogen:CO mole ratio of at least 1:100 and/or the carbon monoxide feed to the carbonylation reactor contains at least 1 mol % hydrogen.

2. A process according to claim 1 wherein the flexibility range of the catalyst is less than 40°.

3. A process according to claim 1 wherein the polydentate ligand is a bidentate ligand or a tridentate ligand.

4. A process according to claim 3 wherein the polydentate ligand is a bidentate ligand of which the two co-ordinating groups each comprise phosphorous as the co-ordinating atom.

5. A process according to claim 4 wherein the two co-ordinating groups are of formula $R^1R^2P$ and $R^3R^4P$ wherein $R^1$, $R^2$, $R^3$ and $R^4$ are each independently selected from unsubstituted or substituted alkenyl groups, alkyl groups and aryl groups.

6. A process according to claim 5 wherein one or more of the aryl groups are substituted or unsubstituted phenyl groups.

7. A process according to claims 5 or 6 wherein $R^1$ to $R^4$ are each a substituted or unsubstituted phenyl group.

8. A process according to any one of claims 1 to 5 wherein the polydentated ligand is selected from the structures of formulas 1 to 3 and 1a

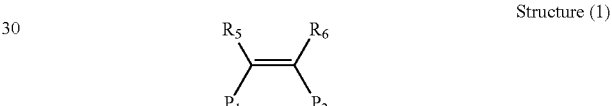

Structure (1)

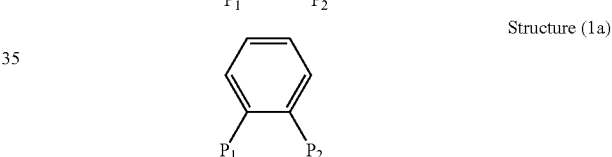

Structure (1a)

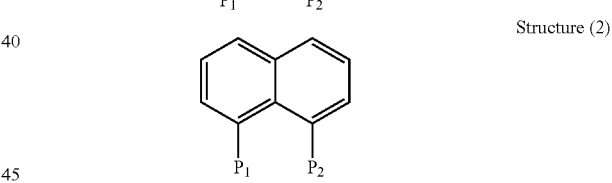

Structure (2)

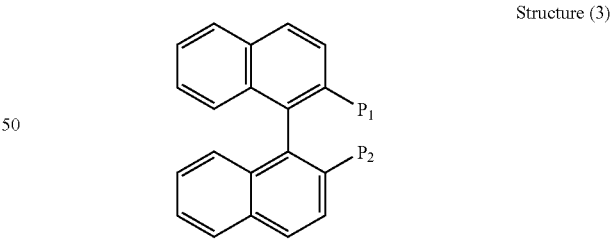

Structure (3)

wherein P1 and P2 are $R^1R^2P$ and $R^3R^4P$ respectively in which $R^1$, $R^2$, $R^3$ and $R^4$ are each independently selected from unsubstituted or substituted alkenyl groups, alkyl groups and aryl groups; $R^5$ and $R^6$ are each independently selected from hydrogen, an alkyl group, an aryl group or may be linked so as to form an aromatic ring.

9. A process according to claim 8 wherein at least one of $R^1$ to $R^4$ is a substituted or unsubstituted phenyl group.

10. A process according to claim 1 or claim 2 in which the polydentate ligand is a tridentate ligand.

11. A process according to claim 10 in which the co-ordinating atoms of the co-ordinating groups are in a meridional co-ordination mode with respect to the rhodium or iridium metal centre.

12. A process according to claim 10 in which the co-ordinating atoms of the co-ordinating groups are in an essentially planar configuration with respect to the rhodium or iridium metal centre.

13. A process according to claim 10 in which the third co-ordinating group has a co-ordinating atom selected from P, As, Sb, oxygen, nitrogen, sulphur and carbene.

14. A process according to claim 13 and wherein two of the co-ordinating groups are as defined in any one of claims 5 to 7.

15. A process according to claim 10 wherein the tridentateLligand is of formula L1($R^7$)L3($R^8$)L2 wherein L1 to L3 are each a co-ordinating group; L1 and L2 each comprising P, N, As or Sb as the co-ordinating atom; $R^7$ and $R^8$ are independently selected from an aryl or an alkenyl group or together form a cyclic structure.

16. A process according to claim 15 wherein $R^7$ and $R^8$ are independently selected from a vinylic and a phenyl group.

17. A process according to claim 15 in which the tridentate ligand co-ordinates to the rhodium or iridium metal centre in a bridging conformation such that L1 and L2 are mutually trans with respect to the metal centre.

18. A process according to claim 15 wherein L1 and L2 each comprise phosphorous as the co-ordinating atom and L3 has a co-ordinating atom selected from oxygen, nitrogen and sulphur.

19. A process according to claim 18 wherein the co-ordinating atom of L3 is oxygen.

20. A process according to claim 18 or claim 19 wherein L1 and L2 are represented by $R^1R^2P$ and $R^3R^4P$ respectively in which $R^1$, $R^2$, $R^3$ and $R^4$ are each independently selected from unsubstituted or substituted alkenyl groups, alkyl groups and aryl groups.

21. A process according to claim 20 wherein each of $R^1$ to $R^4$ is a substituted or unsubstituted phenyl group.

22. A process according to claim 21 wherein each of $R^1$ to $R^4$ is an unsubstituted phenyl group.

23. A process according to claim 15 wherein L1, L2 and L3 are each a nitrogen atom.

24. A process according to claim 10 wherein the tridentate ligand is selected from the group consisting of xantphos, thixantphos, sixantphos, homoxantphos, phosxantphos, isopropxantphos, nixantphos, benzoxantphos, DPEphos, DBFphos and alkyl and aryl derivatives thereof.

25. A process according to claim 24 in which the oxygen atom of the tridentate ligands is substituted by nitrogen or sulphur.

26. A process according to claim 25 wherein at least one of the phosphorous co-ordinating atoms is substituted by an arsenic or antimony atom.

27. A process according to claim 23 in which the tridentate ligand is a substituted or unsubstituted terpyridine.

28. A process according to claim 1 or claim 2 wherein the catalyst comprises rhodium.

29. A process according to claim 1 or claim 2 wherein the catalyst is added to the liquid reaction composition as a performed metal-polydentate ligand complex or is formed in-situ in the liquid reaction composition.

30. A process according to claim 1 or claim 2 wherein the mol ratio of iridium or rhodium metal to polydentate ligand is in the range 1:1 to 1:2.

31. A process according to claim 1 or claim 2 wherein the liquid reaction composition further comprises a catalyst promoter.

32. A process according to claim 31 wherein the promoter is selected from the group consisting of ruthenium, osmium, rhenium, cadmium, mercury, zinc, gallium, indium and tungsten.

33. A process according to claim 1 or claim 2 in which the liquid reaction composition also comprises an effective amount of a compound selected from the group consisting of alkali metal iodides, alkaline earth metal iodides, metal complexes capable of generating I—, salts capable of generating I— and mixtures thereof.

34. A process according to claim 1 or claim 3 wherein the alkyl halide co-catalyst is a $C_1$ to $C_4$ alkyl halide.

35. A process according to claim 1 or claim 2 wherein the alcohol is a $C_1$ to $C_8$ aliphatic alcohol.

36. A process according to claim 35 wherein the alcohol is selected from methanol, ethanol, the propanols and mixtures thereof.

37. A process according to claim 1 or claim 2 wherein the liquid reaction composition comprises water in a concentration in the range 0.1 to 30 wt %.

38. A process according to claim 37 wherein the water concentration is in the range 1 to 10 wt %.

39. A process according to claim 1 in which carbon monoxide and hydrogen are fed separately or as a mixture to the reactor.

40. A process according to claim 39 wherein the carbon monoxide and hydrogen are fed to the reactor as a mixture.

41. A process according to claim 40 wherein the mixture of hydrogen and carbon monoxide is obtained from the reforming of hydrocarbons.

42. A process according to claim 41 wherein the ratio of hydrogen to carbon monoxide is in the range 1.5: to 5:1.

43. A process according to claim 40 or claim 41 wherein the mixture comprises at least 2 mol % hydrogen.

44. A process according to claim 40 wherein the mol ratio of hydrogen to carbon monoxide is in the range 1:100 to 10:1.

45. A process according to claim 1 or claim 2 wherein there is maintained in the process hydrogen at a hydrogen to carbon monoxide mol ratio of at least 1:10.

46. A process according to claim 45 wherein the hydrogen:carbon monoxide mol ratio is at least 1:1.

47. A process according to claim 1 or claim 2 wherein the hydrogen partial pressure is greater than 1 bar.

48. A process according to claim 1 wherein the bite angle is at least 150°.

49. A process according to claim 1 to claim 2 wherein the product of the carbonylation process is selected from acetic acid, methyl acetate and mixtures thereof.

50. A process according to claim 2 wherein the polydentate ligand is a bidentate ligand or a tridentate ligand.

* * * * *